United States Patent
Baeumer et al.

(10) Patent No.: US 8,515,147 B2
(45) Date of Patent: Aug. 20, 2013

(54) SPECTRALLY RESOLVING X-RAY IMAGING DEVICE

(75) Inventors: Christian Baeumer, Aachen (DE);
Roger Steadman Booker, Aachen (DE);
Gereon Vogtmeier, Aachen (DE);
Thomas Scheel, Stolberg (DE);
Christoph Loef, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 779 days.

(21) Appl. No.: 12/518,480

(22) PCT Filed: Dec. 11, 2007

(86) PCT No.: PCT/IB2007/055009
§ 371 (c)(1),
(2), (4) Date: Jun. 10, 2009

(87) PCT Pub. No.: WO2008/072175
PCT Pub. Date: Jun. 19, 2008

(65) Prior Publication Data
US 2010/0008558 A1    Jan. 14, 2010

(30) Foreign Application Priority Data

Dec. 15, 2006   (EP) .................................. 06126200

(51) Int. Cl.
*G06K 9/00*   (2006.01)
(52) U.S. Cl.
USPC ...................................................... 382/131
(58) Field of Classification Search
USPC ......................................... 382/128, 131–132
See application file for complete search history.

(56) References Cited

U.S. PATENT DOCUMENTS

| | | | |
|---|---|---|---|
| 4,686,695 A | 8/1987 | Macovski | |
| 5,661,774 A | 8/1997 | Gordon et al. | |
| 2003/0152189 A1 | 8/2003 | Li et al. | |
| 2004/0264628 A1 | 12/2004 | Besson | |
| 2005/0069086 A1* | 3/2005 | Deych et al. | .................. 378/112 |
| 2005/0084073 A1 | 4/2005 | Seppi et al. | |

FOREIGN PATENT DOCUMENTS

| | | |
|---|---|---|
| JP | 02304898 | 12/1990 |
| JP | 09134794 | 5/1997 |
| JP | 2003325504 | 11/2003 |
| WO | 2006018817 A2 | 2/2006 |
| WO | WO 2006018817 A2 * | 2/2006 |

OTHER PUBLICATIONS

U. Hassler,—"X-Ray Dual-Energy Calibration Based on Estimated Spectral Properties of the Experimental System"—IEEE. vol. 45. No. 3. Jun. 1998, pp. 1699-1712.*

(Continued)

*Primary Examiner* — Matthew Bella
*Assistant Examiner* — Weiwen Yang

(57) ABSTRACT

The invention relates to an X-ray imaging device, particularly a Spectral-CT scanner, that comprises an X-ray source for generating X-radiation with an energy spectrum which varies continuously during an observation period. In a preferred embodiment, the radiation is attenuated in an object according to an energy-dependent attenuation coefficient $\mu$, the transmitted radiation is measured by sensor units of a detector, and the resulting measurement signal is sampled and A/D converted. This is preferably done by an oversampling A/D converter, for example a $\Sigma\Delta$-ADC. The tube voltage that drives the X-ray source is sampled with high frequency. In an evaluation system, these sampled measurement values can be associated with corresponding effective energy spectra to determine the energy dependent attenuation coefficient $\mu$.

20 Claims, 3 Drawing Sheets

(56) References Cited

OTHER PUBLICATIONS

Emil Y. Sidky—"A robust method of x-ray source spectrum estimation from transmission measurements: Demonstrated on computer simulated, scatter-free transmission data" Journal of Applied Physics 97, 124701, 2005, pp. 1-11.*

William C. Barber et al.—"Scintillator Energy and Flux Linearity for RbGd2Br7:Ce, LaCl3:Ce, and LaBr3:Ce"—IEEE, 2003, pp. 936-938.*

David K. Su et al.—"A CMOS Oversampling D/A Converter with a Current-Mode Semidigital Reconstruction Filter"—IEEE journal of solid-state circuits, vol. 28. No. 12, Dec. 1993, pp. 1224-1233.*

Millner—"Determination of effective energies in CT calibration" Med. Phys., 5(6) Nov./Dec. 1978 p. 543-545.*

Cann, C. E., et al.; Postprocessing Dual-Energy CT for Accurate Spinal Mineral Measurement; 1983; Radiology; 149:167.

Heisman, B. J., et al.; Technology and image results of a spectral CT system; 2004; Medical Imaging; vol. 5368:52-59.

Kalender, W. A., et al.; Evaluation of a prototype dual-energy computed tomographic apparatus. I. Phantom studies; 1986; Med. Phys.; 13(3)334-339.

Peppler, W. W., et al.; Total Body Bone Mineral and Lean Body Mass by Dual-Photon Absorptiometry; 1981; Calcif. Tissue Int.; 33:353-359.

Alvarez, R. E., et al.; Energy-selective reconstructions in X-ray Computerized Tomography; 1976; Phys. Med. Biol.; 21(5)733-744.

Fessler, J. A., et al.; Maximum-liklihood dual-energy tomographic image reconstruction; 2002; Proc. of SPIE; 4684:38-49.

Stein et al: "Dual-Energy X-Ray Bone Densitometer Incorporating an Internal Reference System"; Radiology 1987, 165, p. 313.

* cited by examiner

SPECTRALLY RESOLVING X-RAY IMAGING DEVICE

The invention relates to an X-ray imaging device, particularly a Spectral-CT scanner, comprising an X-ray source with a variable energy spectrum. Moreover it relates to a method for the generation of spectrally resolved X-ray images.

X-ray CT systems which employ the energy dependence of the attenuation coefficient μ extend the range of applications compared to conventional CT scanners. Generally, images with enhanced contrast can be reconstructed. The U.S. Pat. No. 5,661,774 describes in this respect a CT scanner with an X-ray tube that can be supplied with two different high voltages in a square wave pattern. Thus X-ray projections of an object corresponding to two different primary photon energy spectra can be obtained. The rapid switching of the high voltages and its synchronization with the detector read-out electronics is however a nontrivial task, particularly if high switching rates shall be achieved.

Based on this situation it was an object of the present invention to provide means for an alternative generation of X-ray images with varying X-ray spectra, wherein it is desirable that the energy resolution is improved and/or the hardware requirements are relieved.

This object is achieved by an X-ray imaging device according to claim 1 and a method according to claim 13. Preferred embodiments are disclosed in the dependent claims.

The X-ray imaging device according to the present invention may in principle be any X-ray apparatus that can generate X-ray projections of an object or images derived therefrom. Preferably, the imaging device is a Computed Tomography (CT) scanner that can reconstruct a sectional image or a 3D image of an object from X-ray projections of this object taken from different directions. The X-ray imaging device comprises the following components:

a) An X-ray source for emitting X-rays with an energy spectrum that varies continuously during a given observation period T. The observation period T typically corresponds to one "frame" in a setup where multiple images ("frames") of an object are taken over a scanning time. Though the following discussion will include the situation that there is just one such observation period T, a multitude of equal observation periods following sequentially in time will typically be present in practice.

b) A detector for producing a plurality of $m \geq 2$ "radiation sampling values", wherein each of these sampling values is indicative of the amount of X-radiation measured by a sensor unit of the detector during a different sampling interval within the observation period.

Measuring the amount of X-radiation by a sensor unit is a process that is well known for (solid-state) X-ray detectors. The sensor unit typically corresponds to one pixel in a two-dimensional array of a large number of similar pixels and comprises some converter unit for converting incident X-ray photons directly or indirectly (i.e. via secondary photons) into an electrical signal, for example a current. The total electrical signal provided by such a sensor unit is then a measure for the intensity of the X-radiation impinging on the sensor unit.

The mentioned different "sampling intervals" may in principle be arbitrarily spread over the observation period T, though an equidistant distribution is usually preferred. Moreover, the relative duration of the sampling intervals (also called "duty cycle") may vary between 0% and 100% of the available time between the beginning of two consecutive sampling intervals.

c) A "spectrum estimation unit" for determining the effective energy spectra $\Phi_k(E)$ of the X-ray source that are associated to the aforementioned sampling intervals. The spectrum estimation unit is typically realized by a digital data processing device like a microcomputer with associated software. Moreover, the "effective energy spectrum" $\Phi_k(E)$ shall reflect the energy distribution of the primary X-ray photons that are emitted by the X-ray source during the corresponding k-th sampling interval ($k=1, \ldots m$). If the sampling interval corresponds for example to just one point in time, the effective energy spectrum will correspond to the instantaneous energy spectrum of the primary X-ray photons at this point in time. If the sampling interval has however some finite duration, the associated effective energy spectrum will be some kind of suitable average over all (varying) energy spectra of the primary X-ray photons that prevailed during the sampling interval.

The described X-ray imaging device has the advantage that it makes use of continuously varying X-ray spectra, which are considerably easier to realize than the quasi-instantaneously changing energy spectra known from the state of the art. The continuously varying spectra imply however that the spectral composition of the primary X-ray beam changes continuously during the sampling intervals in which measurements are made. This problem is overcome by the spectrum estimation unit which determines effective energy spectra for the sampling intervals. The demands on the X-ray generating hardware are therefore relieved at the expense of the data processing effort. In overall, a considerable simplification of the design can however be achieved as the data processing demands can readily be handled by available microcomputers and/or software.

The X-ray source may generate its variable energy spectra in different ways. According to one particular approach, the X-ray source comprises a filter element with time-variable spectral characteristics. The filter element, which is by definition placed into the path of the X-rays emitted by the X-ray source, affects the energy distribution of the originally generated X-ray photons according to its spectral characteristics, wherein said characteristics are variable in time. A particular realization of the filter element comprises for example a rotating disk with variable absorption characteristics (e.g. thickness) in cross sections along its circumference that are sequentially brought into the path of the X-ray photons during the rotation of the disk.

In a practically important design of the X-ray imaging device, the X-ray source comprises an X-ray tube and an associated voltage generator for supplying a periodic tube voltage to the X-ray tube, preferably a sinusoid tube voltage. A continuously varying tube voltage can considerably easier be generated than voltages that rapidly switch between different constant levels. In practice, the temporal change dU/dt of the continuously varying tube voltage U is typically limited to values smaller than 400 kV/ms, preferably smaller than 100 kV/ms, most preferably smaller than 40 kV/ms. This eases the hardware demands and simultaneously allows a variation of the energy spectrum on a shorter timescale. An X-ray source of this kind can preferably be combined with a time-variable filter element of the kind described above to enhance the spectral variation.

In the aforementioned embodiment of the X-ray source, the spectral composition of the emitted X-ray beam varies in relation to the tube voltage supplied by the generator. The imaging device therefore preferably comprises a voltage sensor unit for measuring the tube voltage supplied by the generator. The measurements of this voltage sensor unit can favorably be used by the spectrum estimation unit as they provide in real-time information about the spectrum of the X-ray source that actually prevailed during the sampling intervals.

In a further development of the aforementioned embodiment, the voltage sensor unit comprises a voltage sampling unit for sampling voltage values during the sampling intervals (i.e. the m different intervals within the observation period in which the measured amount of X-radiation is sampled by the detector). The sampling is done according to an associated weighting function g*, which means that each sampled value $U_k$ corresponds to a folding of the signal U(t) with said weighting function g*(t) according to the formula $$U_k = \int U(t) \cdot g^*(t-t_k) dt$$

If the weighting function g* is the delta function δ, the sampling corresponds to the pick-up of an instant value of the signal U. If the weighting function g* is a rectangular normalized pulse, the sampling corresponds to the averaging of the signal U during the pulse duration. In general, the weighting function g is zero outside a limited interval I (g*(t)=0 for all t∉I). The bandwidth of the voltage sampling unit (together with any internal filters) should be sufficiently large to allow precise reconstruction of the tube voltage at any instant of time t, wherein this reconstruction procedure can e.g. be accomplished by interpolation techniques. In particular, the bandwidth of the voltage sampling unit should be at least as high as the bandwidth of the radiation sampling unit which is described below.

In a further development of the aforementioned embodiment, the spectrum estimation unit is designed such that it can determine the effective energy spectra Φ(E) from model spectra that are given for various tube voltages. Using the sampled tube voltages and the model spectra, the spectrum estimation unit can determine the energy spectrum P(E,t) at any instant of time. In a further processing procedure, the energy spectra within a finite interval of time may be combined to yield effective energy spectra Φ(E), e.g. by weighted averaging.

While above the sampling of the tube voltage of an X-ray tube was considered, the following preferred embodiment relates to the sampling process within the detector. In this embodiment the detector comprises a "radiation sampling unit" for sampling the radiation sampling values (that are indicative of the amount of X-radiation measured by the sensor unit) from a continuous measurement signal provided by the sensor unit, wherein this sampling is done during the associated sampling interval according to a weighting function g. If the continuous measurement signal is for example denoted by i(t), the effect of the weighting function g can be described as explained above by the folding operation $$i_k = \int i(t) \cdot g(t-t_k) dt.$$

The weighting function g is typically a symmetric function determined by the read-out electronics that is zero outside the considered sampling interval. In the preferred case that the voltage sensor unit samples voltage values with a weighting function g* and the radiation sampling unit samples radiation sampling values with a weighting function g, the Fourier transform G*(f) of the function g* preferably has equal or higher bandwidth than the Fourier transform G(f) of the weighting function g.

If the spectrum estimation unit is designed such that it can determine the effective energy spectra Φ(E) from model spectra that are given for various tube voltages and if the detector comprises the aforementioned radiation sampling unit with a weighting function g(t), then the determination of the effective energy spectra is preferably done according to the weighting function g(t) of the radiation sampling unit. Based on predetermined model spectra P(E,t) for each time instant t, this determination may for example be done according to the formula $$\Phi_k(E) = \int P(E,t) \cdot g(t-t_k) dt.$$

The voltage sampling unit and/or the radiation sampling unit preferably comprise an oversampling analogue-to-digital converter (ADC), particularly a ΣΔ-ADC. For digital processing, both the analogue tube voltage of the tube and the analogue measurement signal provided by the sensor unit have to be digitized by an ADC. A "normal" A/D converter usually samples a signal x(t) with 100% duty cycle, i.e. every value x(t) of the signal contributes in some way to one of the sampled values. Moreover, the bandwidth of such an ADC is adapted according to the Nyquist criterion. A ΣΔ-ADC, in contrast, can sample the signal x(t) with lower duty cycle (i.e. only a part of the values x(t) between two consecutive sampling times $t_1$, $t_2$ contributes to the sampled values $x_1$, $x_2$ that are associated to said sampling times) and can provide significantly higher bandwidth than required by conventional (CT) signal processing, because it usually operates with an oversampling of the input signal due to internal reasons.

In another preferred embodiment of the imaging device, the voltage sampling unit and/or the radiation sampling unit comprises a filtering unit for generating m data streams, wherein each of these m data streams is composed of (voltage or radiation) sampling values that belong to analogue sampling intervals of different observation periods. If the photon spectrum varies for example periodically over subsequent observation periods, and if radiation sampling values are taken at equidistant radiation sampling intervals during each observation period, then the k-th data stream will be composed of the k-th sampling values of all observation periods (1≤k≤m). Each data stream will therefore correspond to a particular subinterval of the tube voltage.

The imaging device as it was described up to now comprises means for generating X-radiation with a continuously varying spectrum, for generating radiation sampling values corresponding to the detected radiation during radiation sampling intervals, and for estimating effective energy spectra Φ(E) of the radiation during said sampling intervals. The provided information is used in a preferred embodiment of the imaging device by a "spectral discrimination module" that can determine the line integrals $$A_j = \int_L a_j(\underline{r}) \cdot d\underline{r}$$

for a model function $$\mu(E, \underline{r}) = \sum_j f_j(E) \cdot a_j(\underline{r})$$

of the attenuation coefficient μ(E,r) (or $a_j$) in an object located in the X-ray path L between the X-ray source and the detector (or, more precisely, the sensing unit), wherein E is the X-ray photon energy, r is the considered location inside the object, and $f_j$ are given model functions that describe the energy dependence of the attenuation coefficient. The functions $f_j$ may for example be responsible for different effects of photon scattering or for different chemical elements; the coefficients $a_j$ will then describe the corresponding spatial distribution of these effects or elements inside an object and thus comprise the information of interest. The line integrals mentioned above are taken over the X-ray path L from the X-ray source through the object to the associated sensor unit of the detector.

Up to now the discussion of the imaging device made no assumption about a relative movement between an object to be X-rayed and the imaging device. In a particular case, a multitude of "simple" X-ray projection images may therefore be generated with different photon spectra from a resting object located between the X-ray source and the detector with an array of sensor units in the detector. In a preferred embodiment of the invention, the imaging device comprises however a "reconstruction module" for calculating the whole spatial distribution of the aforementioned attenuation coefficient $\mu(E,r)$ in an object located between the X-ray source and the detector from X-ray projections of this object that were taken from different projection directions. Such a reconstruction module can be realized by special hardware or software according to the principles of Computed Tomography that are well known to a person skilled in the art.

The invention further relates to a method for the generation of spectrally resolved X-ray images of an object that comprises the following steps:
a) Emitting X-rays with an energy spectrum that varies continuously during a given observation period.
b) Producing a plurality of $m \geq 2$ radiation sampling values that are indicative of the amount of X-radiation measured in some given measurement region (e.g. of a sensor unit) during different sampling intervals within the observation period.
c) Estimating the effective energy spectra of the X-ray source that are associated to the aforementioned sampling intervals.

The method comprises in general form the steps that can be executed with an imaging device of the kind described above. Therefore, reference is made to the preceding description for more information on the details, advantages and improvements of that method.

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

Figure 1:
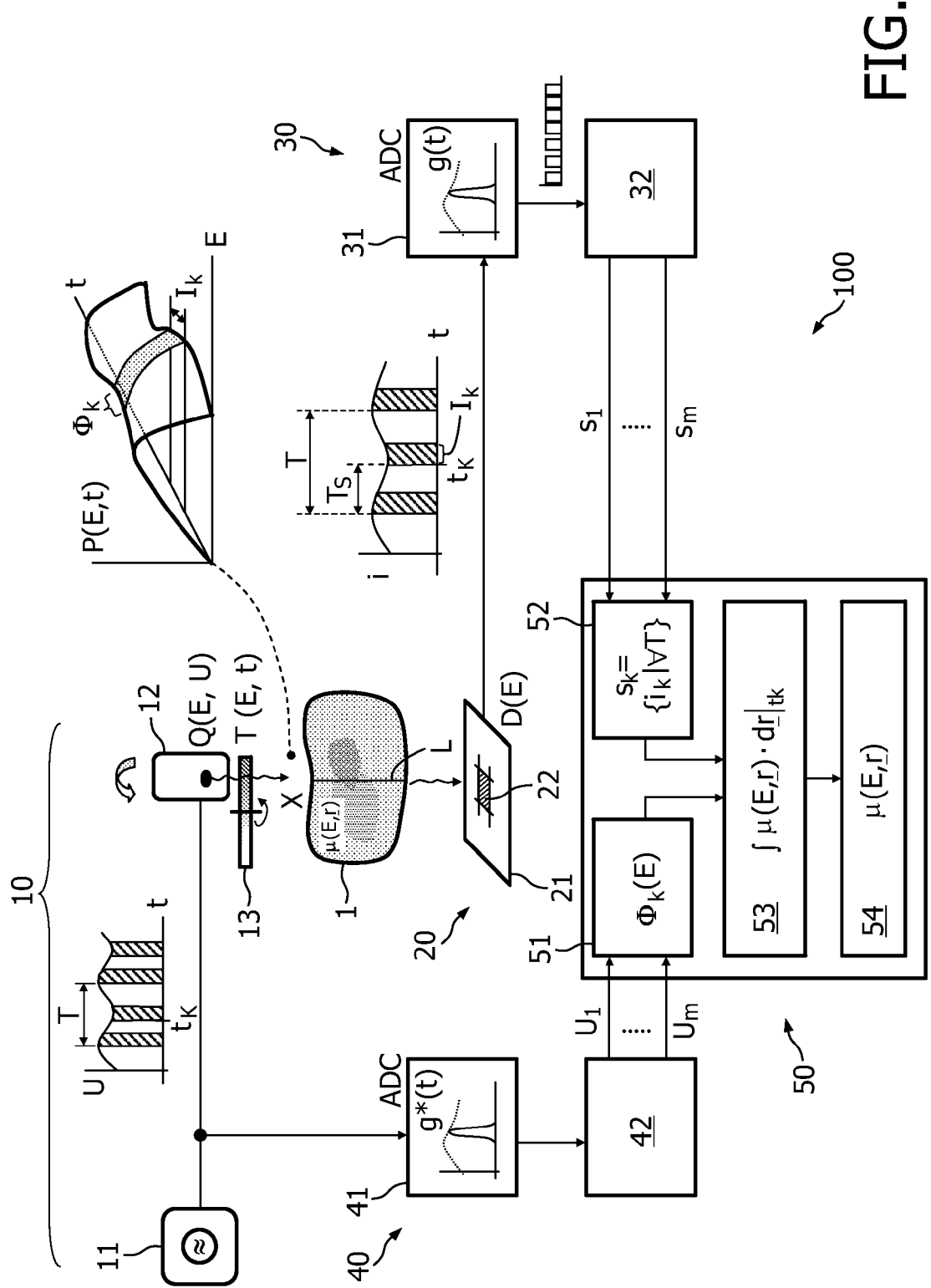
FIG. 1 is a schematic illustration of an imaging device according to the present invention.

The key hardware components of nowadays X-ray Computed Tomography systems are an X-ray tube which generates a polychromatic X-ray spectrum and a detector. The upper limit of the primary spectrum of X-ray tubes is given by the applied high voltage (typically 120 keV-140 keV). Detectors for CT measure the integrated charge generated by interactions of X-ray photons and secondary radiation with a sensor material. The measurements in a multitude of differently oriented projections then provides information on the attenuation of the transmitted X-ray radiation, described by an attenuation coefficient g.

The attenuation coefficient $\mu$ is generally dependent on the energy of the X-ray photon traversing the matter. Nowadays CT scanners do not account for the energy dependence of the attenuation coefficient $\mu$ and so-called beam-hardening artifacts may occur. In contrast to this, spectral-CT systems are designed to exploit the energy dependence of the attenuation coefficient $\mu=\mu(E,r)$, resulting in higher contrast (e.g. in energy-weighting techniques), material decomposition, or enhanced selectivity for contrast agents through K-edge imaging.

There are several options to implement a Spectral-CT system (see e.g. B. J. Heismann, S. Wirth, S. Janssen, Q. Spreiter, "Technology and image results of spectral CT system", Proc. SPIE 5368, 2004, 52-59).

The "dual kV" method is a particular realization of a Spectral-CT system, wherein projection data are recorded at two different voltage settings (i.e. two different primary X-ray spectra). The "multi kV" method is an extension of the dual kV method with three or more high-voltage settings. Imaging with two or more high-voltage settings is sometimes referred to as "tomochemistry". The major applications for dual-energy radiography are accurate and precise bone measurements with dual-photon absorptiometry (DPA) (cf. Peppler and R. Mazess, "Total body bone mineral and lean body mass by dual-photon absorptiometry, I. Theory and measurement procedure", Calcif. Tissue Int. 1981, 3:353-359) and dual-energy X-ray absorptiometry (DEXA, cf. Stein, M. Walthman, J. Lazewatsky and A. Hochberg, "Dual energy X-ray bone densitometer incorporating an internal reference system", Radiology 1987, 165: 31 3), as well as dual-energy Computed Tomography (DECT, cf. Cann, H. Genant, B. Rutt, and B. Stebler, "Postprocessing dual-energy CT for accurate spinal mineral measurement", Radiology 1983, 149:167).

The following approaches can be used to realize the dual kV or multi kV method:

Several consecutive scans (i.e. rotations around the object) with different high-voltage settings are made. Image quality may in this case be deteriorated by artifacts from patient motion.

Fast switching is done between the different high-voltage settings during scanning with the X-ray detector recording projections for each rotation angle and high-voltage setting (cf. W. A. Kalender et al., "Evaluation of a prototype dual-energy computed tomographic apparatus, I. Phantom studies", Med. Phys. 13 (1986) 334-339).

Two (or more) X-ray tubes and two (or more) detectors are mounted on the gantry and operated simultaneously during scanning.

Regarding the technical implementation of a rapid high-voltage switching system, a matching in the time domain between the high-voltage modulation and the detector in conjunction with its A/D converter is required. When an integration mode (or current mode) is assumed for the detector of a multi-kV system, all charge generated in an X-ray sensor during a frame time T is integrated. This is a boxcar-type windowing in the time domain, i.e. there are sharp transitions between time frames. Rapid switching between two (or more) high-voltages in a square-wave manner complies with this notion.

The current invention proposes a special realization of a Spectral-CT system. It can, thus, enable higher contrasts than usual CT depending on the application. This holds especially for the case that two or more materials in an object have to be separated. In some applications this material can be a contrast agent. As a by-product, beam-hardening can be easily corrected for. The invention addresses some of the problems and challenges associated with prior switching techniques of the tube high-voltage in CT. In particular, strong transients shall be avoided in the high-voltage switching unit. The proposed system preferably needs only one high-voltage generation unit. Further, an elaborated matching in time between the high-voltage switching control and detector sampling prior to a scan or during scanning is not necessary.

FIG. 1 is a schematic diagram that illustrates an X-ray imaging device 100, for example a CT scanner, according to the present invention. This imaging device 100 comprises the following main components:

- An X-ray source 10 for generating X-radiation with a continuously (and preferably also periodically) varying energy spectrum P(E,t).
- A detector that is composed of a sensor part 20 for measuring X-radiation emitted by the X-ray source 10 and for providing a corresponding continuous measurement signal i(t), and of a read-out part 30 for reading out said measurement signal i(t) and for converting it into digital values.
- A voltage sensor unit 40 for measuring the actual tube voltage U(t) in the radiation source 10.
- An evaluation system 50, preferably realized by a data processing device like a workstation, to which the sensed and digitized tube voltages and the detector measurements are supplied for further processing.

An object to be X-rayed, e.g. the body 1 of a patient, is placed between the X-ray source 10 and the sensor part 20 of the detector such that the transmission of the X-radiation through this object is measured in the detector. The aforementioned main components of the imaging device 100 will now be described in more detail.

The X-radiation source 10 comprises a voltage generator 11 that supplies a tube voltage U(t) to an X-ray tube 12. The constant high-voltage for the X-ray tube used in state-of-the-art CT scanners is here substituted by a modulated high-voltage U(t). The modulation is preferably a sinusoid at frequency $f_1=1/T$, with T being the "observation period" or frame time, or a sinusoid with a limited number of harmonics of frequency $n \cdot f_1$ (n=2, 3, 4, ...). Depending on the particular hardware that is used for the X-radiation source 10, a typical value for the voltage increase dU/dt is 150 kV/ms and for the voltage decrease 40 kV/ms. Maximal values for dU/dt are currently in the range of 400 kV/ms.

In the tube 12, X-ray photons are generated by processes well known in the art. The energy spectrum of these photons depends on the tube voltage U according to some function Q(E,U) that can be modeled e.g. from theoretical considerations or measurements.

The X-ray source 10 further comprises a disk 13 that rotates about an axis that is parallel to an isoray (i.e. to the optical path of the tube 12) and that has varying characteristics along its circumference. When the X-radiation passes through a point on this circumference, it sees a time-variable spectral transmittance T(E,t) due to the rotation of the disk. The combination of the X-ray tube 12 (driven with the modulated voltage U(t)) with the rotating filter 13 then results in a time-variable energy spectrum P(E,t) of the X-ray photons X finally emitted by the radiation source 10. This spectrum is schematically indicated in the Figure. The angular frequency $f_R$ of the disk rotation is preferably synchronized to the modulation frequency $f_1$ of the tube voltage, i.e. $f_1 = n \cdot f_R$ (n=1, 2, 3, ...). The depth profile of the disk has then a similar frequency content as the modulation of the high-voltage. In that way the disk 13 acts as an X-ray filter yielding stronger spectral changes during one period. For instance, in a sampling unit with 100% duty cycle, i.e. uniform averaging of samples values, the realization could be a rotating metal disk which has a regular pattern of holes ("chopper").

The radiation emitted by the X-ray source 10 next passes through the object 1, wherein the effect of this object on the radiation can be described by the spatially varying attenuation coefficient μ(E,r), with r being the location inside the object. In the described setup, the energy dependence of this coefficient is of interest, too. In a modeling approach, the attenuation coefficient can be expressed by a sum $$\mu(E, r) = \sum_j f_j(E) \cdot a_j(r)$$

in which the $f_j(E)$ describe different energy dependences (obtained e.g. from theoretical considerations) and the $a_j(r)$ describe the spatial distribution of these dependences within the object that shall be determined by the X-ray procedure. Particular modeling examples will be described in more detail below.

The sensor part 20 of the detector comprises a plurality of sensor units 22 or "pixels" that are distributed in a two-dimensional array across a sensor area 21. In the following, only the read-out and data processing for one such sensor unit 22 will be considered, but it has to be kept in mind that usually a large number of pixels has to be read-out and processed for each projection image (frame). In the sensor unit 22, the X-radiation that impinges on it is converted into an electrical signal according to some sensor specific spectral energy response D(E). The electrical signal that corresponds to the amount (intensity) of absorbed X-radiation is denoted in the following as i(t). It may for example correspond to a photo current.

The detector signal i(t) varies with the "observation period" T according to the periodic variation of the tube voltage U(t). An additional variation of the detector signal i(t) is typically introduced by a relative movement between the object 1 and the imaging device 100, wherein this movement usually takes place on a coarser timescale (in the order of the observation period T).

In theory it would be possible to take at some time instant $t_k$
- the measured detector signal $i(t_k)$,
- the associated tube voltage $U(t_k)$,
- and the transmittance $T(E,t_k)$ of the rotating disk 13, for calculating the X-ray spectrum $\Phi_k(E)=P(E,t_k)$ that prevailed at the time $t_k$, and associating this spectrum $\Phi_k(E)$ to the measured detector value $i(t_k)$.

If this would be done for different time instances $t_1, \ldots, t_k, \ldots t_m$ during the observation period T, this would yield measurement values $i(t_k)$ corresponding to different photon energy spectra $\Phi_k(E)$.

In practice, the aforementioned procedure is hardly feasible due to the limited capabilities of available hardware components. A more realistic approach has therefore to take into account that the measurement signal i(t) is sampled over finite sampling intervals (or duty cycles) $I_k$ with a temporal weighting function g(t) that is determined by the used sampling electronics. As will be described in more detail below, an oversampling A/D converter 31 is preferably used for sampling the measurement signal i(t) during m≦2 time intervals $I_1, \ldots I_k, \ldots I_m$ that start at times $t_1, \ldots t_k, \ldots t_m$ during a considered observation period T. If a ΣΔ-ADC is used for this purpose, its output corresponds to a pulse density modulated (PDM) bit stream that is further processed by some filter unit 32.

The filter unit 32 generates for example m data streams $s_1, \ldots s_k, \ldots s_m$ from the ADC output and provides them to the evaluation system 50. Each of these data streams $s_k$ consists of radiation sampling values $i_k$ that correspond to equivalent sampling times $t_k$ of consecutive observation periods T.

The tube voltage U(t) is sampled in a similar way as the measured detector signal i(t) by some ADC 41 combined with a filter unit 42. Preferably, this ADC 41 and filter unit 42 have the same or higher bandwidth as the ADC 31 and filter 32 used for preprocessing of the detector read-out i(t), and the tube voltage U(t) is sampled in the same time intervals $I_k$ with some weighting function g*(t).

The sampling values $U_1, \ldots U_k, \ldots U_m$ of the tube voltage are supplied as m data streams to a "spectrum estimation module" 51 within the evaluation system 50. In this spectrum estimation module 51, effective energy spectra $\Phi_k(E)$ are determined that describe the spectra of X-radiation which effectively prevailed during the sampling intervals $I_k$. The effective energy spectra $\Phi_k(E)$ can for example be determined from the (modeled) primary spectra P(E,t). They may particularly correspond to a weighted temporal average of the primary spectra P(E,t), wherein the weighting function g(t) is the same as that with which the detector signal i(t) is sampled. This guarantees that each instantaneous input P(E,t) of primary X-ray photons is taken into account with the same weight as the resulting detector measurement signal i(t).

In a "spectral discrimination module" 53 of the evaluation system 50, the effective energy spectra $\Phi_k(E)$ and the radiation sampling values $i_k$ are combined to determine the line integrals of the attenuation coefficient $\mu(E,r)$ along the ray path L through the object 1 for the m different times $t_k$ in each observation period T. These integrals are necessary for the determination of the above mentioned spatial distribution functions $a_j(r)$ of the attenuation coefficient $\mu(E,r)$.

The double arrow above the tube 12 indicates that this tube (and synchronously also the detector) usually rotates around the object 1 to generate projections of it from different directions that allow a reconstruction of cross sections through the object. Such a reconstruction is done in the "reconstruction module" 54 based on all line integrals determined during a complete scan (i.e. a sweep of radiation source and detector around the object 1). The spatial distribution of the attenuation coefficient within the object can further be used for the generation of spectrally weighted images according to the known principles of Spectral-CT.

When the processing of the signals i(t) from the X-ray sensor material is performed by an ADC 31 with high bandwidth, information on the energy dependence of the X-ray absorption $\mu(E,r)$ is encoded in the spectral content of the ADC output data. If one is interested in a multi-kV system with $m \geq 2$ high-voltage settings (e.g. m=2 for the dual energy mode), then the bandwidth of the ADC has to be $m \cdot f_1$ with $f_1=1/T$ being the frequency of the modulated tube voltage U(t). As described above, the ADC output data with sampling frequency $f_s=m \cdot f_1$ are—in the most simple operation mode of the filter unit 32—fanned out to m output data streams, each of these m outputs is subject to a phase shift or latency $\Delta T_k < T$, and each output is finally downsampled to $f_1$. In this way each output $s_k$ represents a detector signal corresponding to a unique high-voltage setting. In contrast to the known implementations of rapid kV switching, these high-voltage settings do not correspond to a single value for the upper high-voltage (kVp). It is rather a mixture of high-voltage settings with similar peak values due to the filter operations. However, the effective spectra $\Phi_k$ can be calculated by models or by models in conjunction with the monitored high-voltage values.

It is preferred to sample the high-voltage U(t) with an ADC that features similar or higher bandwidth as the kind of ADC which samples the signal i(t) of the detector pixels. In that way, the effective kVp's are available in real-time. Similarly, the models for the X-ray spectra with different kVp's can be determined with the same operations as being performed in the ADC, because it is straightforward to transform the digital filter operations to software.

Moreover, it is possible that the frame frequency $f_1=1/T$ is dynamically defined by a user. The frequency response of the ADC converters 31, 41 including filter units 32, 42 can be easily adapted by loading for a new $f_1$ another set of filter coefficients in the filter unit. It is, thus, possible to trade spectral resolution (determined by the number m of discriminated high-voltage settings) for resolution in readout speed (i.e. the length of the observation period T) and vice versa. A similar argument holds for aliasing artifacts.

In later processing stages, i.e. prior to/after preprocessing or reconstruction the information from all output data streams $s_k$ is used to calculate tomograms which have a spectral weighting. Methods to derive those tomograms from the set of measured projection data are described in literature (e.g. R. E. Alvarez, A. Macovski, "Energy-selective reconstructions in X-ray Computerized Tomography", Phys. Med. Biol., 1976, Vol. 21, No. 5, 733-744; J. A. Fessler et al., "Maximum-likelihood dual-energy tomographic image reconstruction", Proc. of SPIE 4684 (2002), 38-49). In the article of Alvarez and Macovski, projections with different high-voltage settings are transformed to another set of base functions. The base functions could, e.g., represent materials within the scanned object.

To provide high voltages for the X-ray tube 12, high frequency-switching generators can be used. These generators consist of a high frequency inverter, a high voltage step-up transformer, and a high voltage rectifier (cf. EP 716 561). Due to the small energy storage components required when switching at high frequency, a fast change of the output voltage can be achieved. A controlled voltage rise either linear or non-linear (sinusoidal) can be achieved. The voltage decay can only be achieved when the X-ray tube is active and the X-ray tube current discharges the storage capacitors. The linear or non-linear discharge is controlled by means of the energy provided to the high voltage rectifier stack during this time instant. The modulation frequency of a sinusoidal voltage component depends on the amount of energy storage at the high voltage rectifier. With increasing operating frequencies the amount of storage elements is reduced and thus high modulation frequencies and/or higher amplitudes are possible. The high voltage cable between the high voltage generator and the X-ray tube limits the voltage rise and fall, too.

Figure 2:
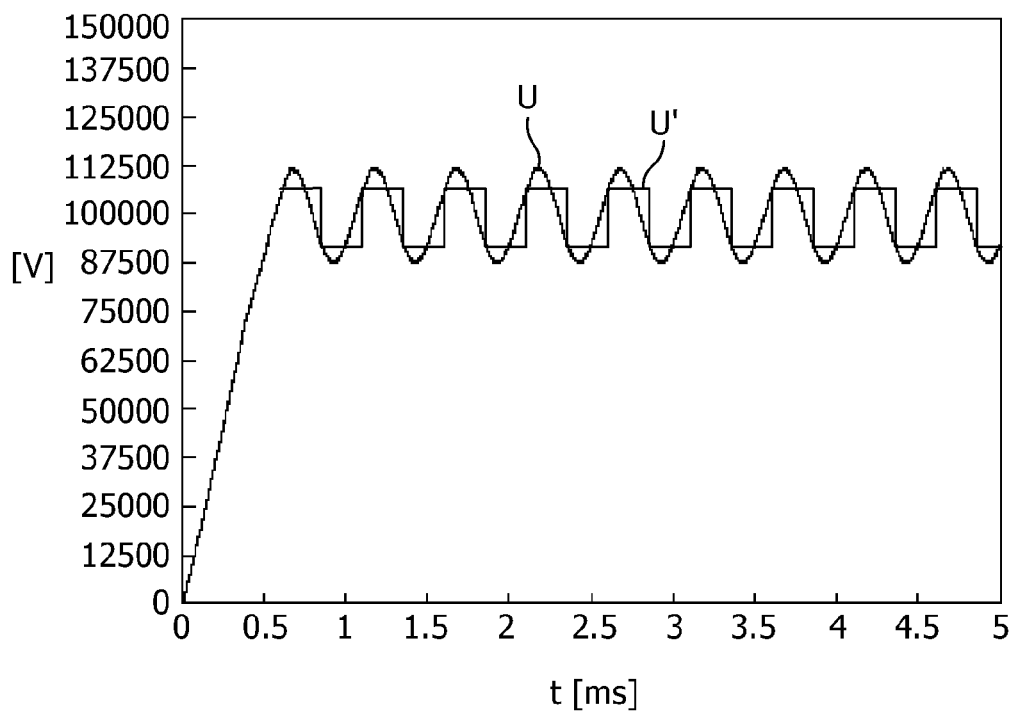
FIG. 2 shows a typical tube voltage according to the present invention and according to the prior art.

FIG. 2 shows a typical course of a tube voltage U (100 kV±15 kV; vertical axis) over time t, wherein the tube voltage is modulated with a switching frequency of 2 kHz for a high frequency generator with a 1 m high voltage cable and a tube current of 240 mA. Moreover, the curve U' of a rapid binary switching between two high-voltage settings with strong transients according to the state of the art is shown in the diagram. This is visualized in idealized form, i.e. as a square wave. It should be noted that the transients between high-voltages correspond to the limits of the time frames which are the integration limits in the corresponding detector readout system.

If higher modulation frequencies and/or modulation amplitudes are required, a stacked high voltage generator topology can be used.

Figure 3:
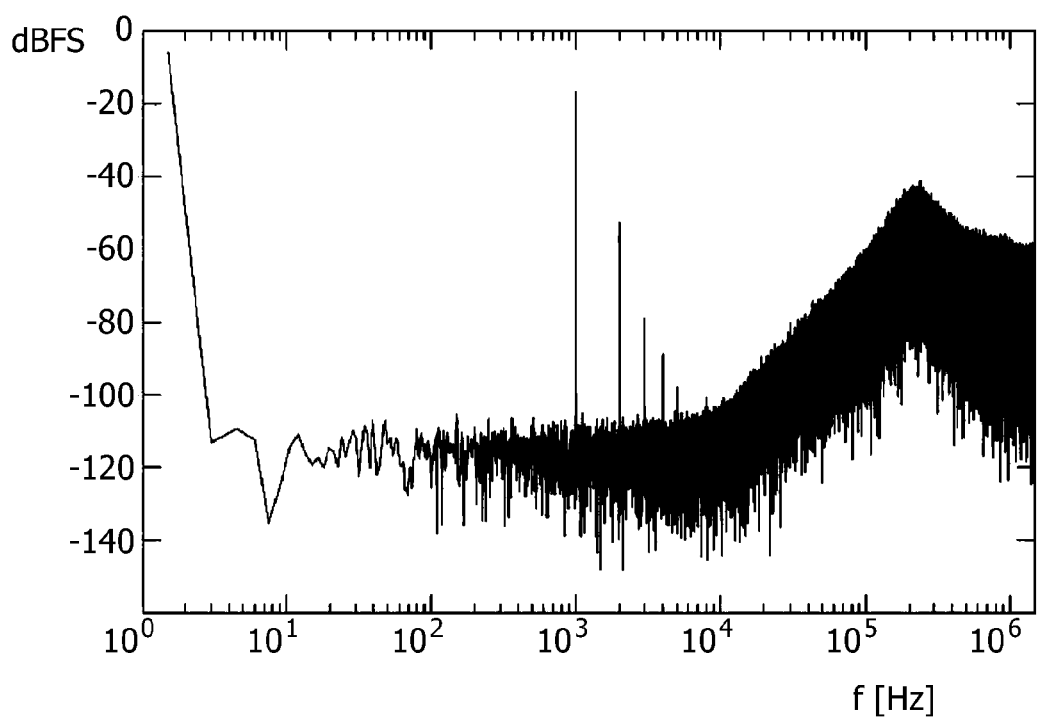
FIG. 3 shows an exemplary output spectrum of a $\Sigma\Delta$-modulator to which a 1 kHz sinusoid with some harmonics have been applied as input.

It was already mentioned that a $\Sigma\Delta$-type ADC (also called $\Delta\Sigma$-ADC) can be employed as a realization of an A/D converter which covers the dynamic range of the application and provides higher bandwidth than necessary in conventional CT (cf. S. R. Norsworthy, R. Schreier, and G. C. Temes, "Delta-Sigma data converters: theory design and simulations", IEEE Circuits & Systems Society). A typical frequency spectrum of a Sigma-Delta-modulator to which a 1 kHz sinusoid with some harmonics have been applied as input is shown in FIG. 3. The modulator is a special kind of oversampling ADC with noise-shaping functionality. In the above example one could e.g. take $f_1=2$ kHz. The extra "band" for the spectral encoding would be between 2 kHz and about 10 kHz. Although noise increases with higher frequencies, the spectral band could be extended to higher frequencies (multiples of 10 kHz in the example). That part of the frequency spectrum would, however, have a limited signal-to-noise ratio.

The technical implementation of the filter units 32, 42 can be done with standard methods. In particular, filtering can be performed with field-programmable gate arrays (FPGAs), digital signal processors (DSPs) or digital application-specific integrated circuits (ASICs).

In the following, a more detailed description of a typical data processing will be given. In this context, the frequency response of the oversampling ADC 41 is denoted as G(f), the corresponding impulse response as g(t).

The current i(t) of a single detector pixel 22 is sampled at frequency $f_s=m \cdot f_1$, $(f_1=1/T)$. Thus G(f)=0 for $f>f_s/2$ if the sampling theorem is fulfilled. The sampled and quantized values are denoted as y(t), $y(t+T_s)$, $y(t+2T_s)$, ... with $T_s=1/f_s$. The high-voltage which is applied to the X-ray tube is assumed to have a time-varying waveform with period T': U(t)=U(t+T').

In case of a rapid switching between two high-voltages, U(t) is a square wave with some time offset $t_0$. The obvious consequence for implementation of such a system is that sampling has to be matched in time with the voltage switching, i.e. T=T' and $t_0$ has to be adjusted accordingly. This time synchronization could, e.g., be achieved with a master clock which drives the clock for data readout and for high-voltage switching. The period T is then subdivided into $m \geq 2$ sub-periods of length $T_b=T/m$. If sampling of the signal from the X-ray sensor with frequency $f_s$ is performed with 100% duty cycle (i.e. the intervals $I_k$ in FIG. 1 would contact each other), the frequency response of the corresponding signal processing electronics is a sinc-function with a zero at $1/f_s$.

The approach proposed here provides a general scheme to realize a rapid high-voltage switching with arbitrary waveform. As outlined above, this waveform can be optimized to reduce the hardware costs for high-voltage switching, wherein a preferred waveform is a sinusoid.

The following procedure is a generic algorithm for the acquisition and analysis of rapid-kVp switching data (assuming that T=T', $T_s=T/m$):

For $t_A=0$ to End_of_Scan in steps of T do *** sample continuously over scan time
For k=1 to m do *** sub-sampling during each period T $t=t_A+k \cdot T_s$ a) record y(t),
b) determine U(t),
c) determine effective primary tube spectrum $\Phi_k(E)$ from b) endfor
d) determine coefficients $a_j(t_A)=1 \ldots J)$ according $\mu(E,\underline{r})$ model
(e.g. method of Alvarez-Markovski)
endfor The method of Alvarez-Markovski that can be applied in step d) can be summarized as follows (cf. cited article R. E. Alvarez, A. Macovski;):

The evaluation of spectral data is based on the decomposition of the attenuation coefficient g into, e.g., Photo-effect-, Compton-effect- and K-edge-material-components:

$$\mu(E, \underline{r}) = \sum_{j=1}^{3} f_j(E) \cdot a_j(\underline{r})$$
$$= \frac{1}{E^3} a_1(\underline{r}) + f_{KN}(E) \cdot a_2(\underline{r}) + \mu^*_{Ke}(E) \cdot a_3(\underline{r})$$

The three line-integrals $$A_j = \int_L a_j(\underline{r}) \cdot d\underline{r}$$

taken along the X-ray path L through an object 1, which appear in the measurement signal of a sensor unit 22, are obtained by solving (e.g. through Maximum Likelihood estimation) a system of non-linear equations. It should be noted that the base functions $f_j$ of $\mu(E,\underline{r})$ could also represent the absorption in two different materials of the object, e.g. water and calcium.

In case of the tube voltage switching, the method of Alvarez-Markovski looks as follows:

$$i_k = \int S_k(E) \cdot \exp\left\{-\frac{1}{E^3}A_1 - f_{KN}(E) \cdot A_2 - \mu^*_{Ke}(E) \cdot A_3\right\} dE,$$
$$k = 1, 2, \ldots m$$

where the $S_k(E)$ represent the different primary spectra $\Phi_k(E)$ multiplied by the detector response D(E). Assuming a detective quantum efficiency of 100%, $S_k(E)=\Phi_k(E)$.

As mentioned above, for a square-wave switching of the tube voltage it is assumed that the sampling interval $T_s$ is synchronized to the interval $T_b$ during which the high-voltage has its upper or lower value. The module b) of the generic algorithm can then be realized by either employing the set point of the high voltage at time t, or by monitoring the applied voltage U at time t. The corresponding effective primary tube spectrum $\Phi_k(E)$ in step c) is, for instance, calculated with a model applied at time t. Module c) can be calculated in this case prior to a scan or can be part of the firmware, so that execution of module c) is a retrieval of this tube spectral data.

To incorporate arbitrary shapes of the high-voltage switching sequence, the following measures have to be taken:

Sampling of the detector signal i(t) in step a) of the generic procedure is performed with an ADC with frequency response G(f).

The tube high voltage U(t) in step b) of the generic procedure is determined with a signal processing unit which has the same bandwidth or higher bandwidth.

The effective primary tube spectrum $\Phi_k(E)$ in step c) of the generic procedure is calculated accordingly. In contrast to the square-wave case where this spectrum has a single peak energy (i.e. a single high voltage), the primary spectrum corresponding to one sampling interval $I_k$ now represents a distribution of peak energies. In the case where signals i(t) are sampled with 100% duty cycle, i.e.

the impulse response g(t) has a rectangular ("boxcar") shape, $\Phi_k(E)$ represents the mean of the primary tube spectra P(E,t) with peak energies $E_{peak}$ in some interval $E1<E_{peak}<E2$.

If the signal processing electronics G(f) has a flexible frequency response, the impulse response g(t) might deviate significantly from the boxcar shape. In this case the calculation of $\Phi_k(E)$ for a sampling point $t_k$ is a weighted average (i.e. weighted by g(t)) of tube spectra.

Two alternative methods are proposed here to calculate the weighted average of tube spectra in the aforementioned case:
Method 1:

A continuous-time model of the tube voltage $U_{model}(t)$ is constructed and combined with a tube spectrum model Q(E, U). Folding the resulting tube spectrum model P(E,t) with the impulse response of the detector, g(t), finally gives a theoretical spectrum $\Phi_k(E)$ for every tube voltage U(t) from execution of module b). It is important to note that this rather complicated procedure has to be performed and the spectrum $\Phi_k(E)$ cannot be calculated by taking the spectrum corresponding to the peak energy $E_{peak}$ at the sampling time t, because the filter operations require a linear-time invariant system (LTI system) and the energy dependence of the X-ray transmission is non-linear.

This method can be applied if the waveform of the tube voltage switching is symmetric (g(t) has to be symmetric in X-ray CT, because linear-phase filters are required; linear phase, in turn, is mandatory because the phase corresponds to the rotation angle of the gantry which is transforms to spatial information after reconstruction).

Figure 4:
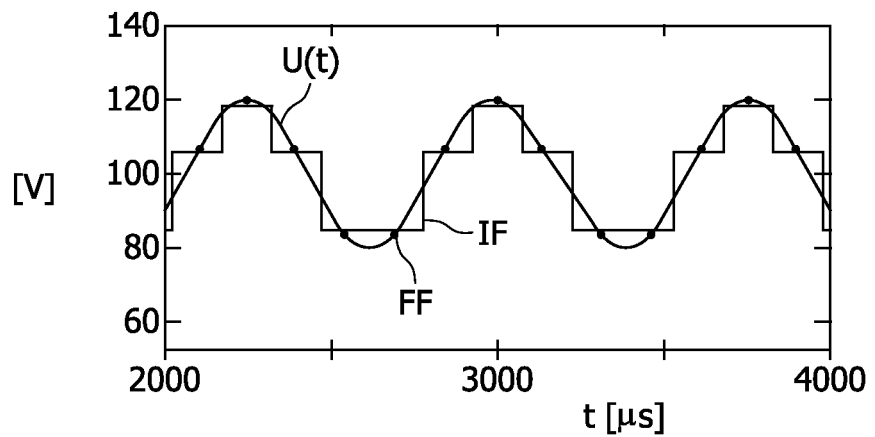
FIG. 4 shows the tube voltage modulation of an X-ray tube and its sampling by a flexible filter and an integration filter, respectively.
Figure 5:
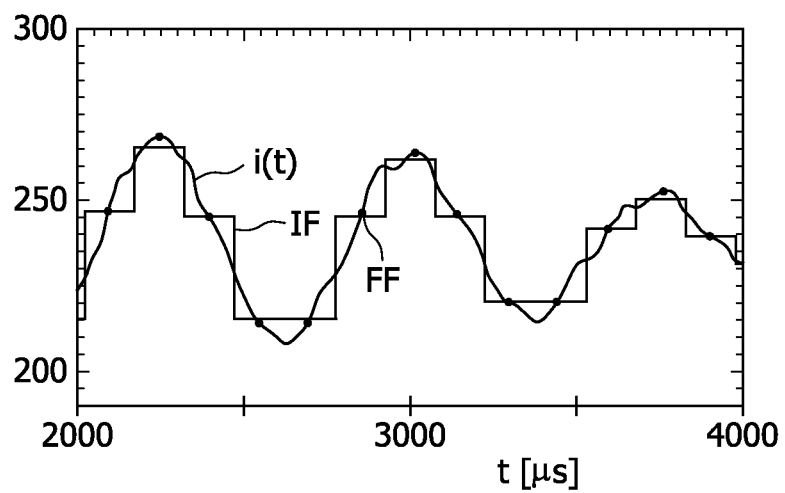
FIG. 5 shows the detector output resulting from the tube voltage of FIG. 4 and its sampling by a flexible filter and an integration filter, respectively.

If a rotating disk 13 is mounted between X-ray tube and object and if the frequency of the rotation is equal to the frequency $f_1$ of the high-voltage modulation, the primary spectrum $\Phi_k(E)$ will be modified by the transmission characteristics of the rotating disk. As for the high voltage, a continuous-time model for the transmission T(E,t) is established and multiplied by the corresponding tube spectrum to yield P(E,t) for this case. Again, folding with g(t) gives the resulting effective spectrum $\Phi_k(E)$ for the sampled data under consideration. T(E,t) is preferably chosen such that the resulting effective spectra $\Phi_k(E)$ are as orthogonal as possible.
Method 2:

The second method is a special case of Method 1 where G(f) has a boxcar shape. This means that sampling of i(t) and U(t) is performed with minimum duty cycle (→0%). This is visualized in FIGS. 4 and 5, which show an exemplary operation of a Spectral-CT system with high-voltage modulation U(t) (FIG. 4) and the corresponding detector output i(t) (FIG. 5). Two kinds of signal processing electronics are considered. First, sampling is performed with an integrator-type filter IF, i.e. signals are averaged over an integration period. Second, a flexible filter FF, which has in this example a boxcar shape in the frequency domain, is applied, i.e. the sampled data point at time t reflects the quantized data value at the time instant t.

The spectrum $\Phi_k(E)$ is calculated as in Method 1. The advantage of Method 2 is that because of the uniform response of G(f) and the resulting low duty cycle of the sampling the signal of the detector can be reconstructed ("interpolation") with high precision at any point in time t. This can be performed with standard methods of digital signal processing. Thus, there is no need to adjust the phase relation to between high-voltage modulation and sampling of the detector signal. It should be noted that in X-ray CT a sinc-type frequency response G(f) is preferred. Thus, an additional filter operation G(f) is applied to y(t) after interpolation and, as in the previous method, to the continuous-time model $U_{model}(t)$.

Method 2 described above can also be used to get rid of the constraint T=T'. If it is assumed that sampling of detector data and tube switching are not perfectly synchronized, but that T≈T', on average the same spectral information is available as for T=T'. Further, no tuning of the phase to will be necessary.
Method 3

In a third Method 3, a higher number of data points is used for the sub-sampling of m detector data than for the number n of coefficients that will be extracted with the Alvarez-Markovski method: $A_1, \ldots A_n$ with m>n. Otherwise the same technique is used as in Method 2. As a final step, the maximum-likelihood method is applied to extract the coefficients $A_1, \ldots A_n$ (cf R. E. Alvarez, A. Macovski, above). For instance, for n=2, $A_1$ and $A_2$ could represent the "photoeffect image" and the "Compton-effect image", respectively, where the latter image allows for an quantitative measurement of the electron density.

It is stressed again that Method 3 requires no synchronization between high-voltage switching and X-ray detector. Generally, the switching waveform can be chosen for maximum high-voltage modulation depth which roughly corresponds to a maximum of orthogonality between the sub-sampled detector signals. It is emphasized that after sampling of the detector data and the tube voltage with a detector converter which has approximately a boxcar-type frequency response G(f), standard methods of digital signal processing can be applied to pre-process the data in order to achieve optimum image quality, including spectral information.

The systems and methods described above can be used in any field of imaging, for example:
- In medical imaging where X-ray CT systems are currently used. Many clinical applications will benefit from the enhanced contrast resolution, particularly if the system is combined with contrast agents. In CT-angio, calcifications can be made better visible.
- In non-destructive testing, because material de-composition can be performed in the processing stages.
- In homeland security to make baggage-scanning systems more selective to materials.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An X-ray imaging device, particularly a CT scanner, comprising:
   an X-ray source for emitting X-rays with an energy spectrum that varies continuously during a given observation period;
   a detector for producing a plurality of m≧2 radiation sampling values that are indicative of the amount of X-radiation measured by a sensor unit of the detector during different sampling intervals within the observation period; and
   a spectrum estimation unit for determining effective energy spectra of the X-ray source that are associated to the sampling intervals, wherein the spectrum estimation unit determines the effective energy spectra by folding a tube spectrum model, which is generated based on a continuous-time model of a tube voltage of the X-ray source combined with a tube spectrum model, with an impulse response of the detector.

2. The X-ray imaging device according to claim 1, wherein the X-ray source comprises a filter element with time-variable spectral characteristics.

3. The X-ray imaging device according to claim 1, wherein the X-ray source comprises an X-ray tube and an associated generator for supplying a periodic tube voltage to the X-ray tube, preferably a sinusoid tube voltage.

4. The X-ray imaging device according to claim 3, wherein the device comprises a voltage sensor unit for measuring the tube voltage.

5. The X-ray imaging device according to claim 4, wherein voltage sensor unit comprises a voltage sampling unit for sampling voltage values during the sampling intervals.

6. The X-ray imaging device according to claim 5, wherein the spectrum estimation unit determines the effective energy spectra from model spectra, which are given for various tube voltages.

7. The X-ray imaging device according to claim 1, wherein the detector comprises a radiation sampling unit for sampling the sampling values from a continuous measurement signal according to an associated weighting function.

8. The X-ray imaging device according to claim 6, wherein the spectrum estimation unit determines the effective energy spectra according to the weighting function of the radiation sampling unit.

9. The X-ray imaging device according to claim 5, wherein the voltage sampling unit and/or the detector comprises an oversampling A/D-converter, particularly a $\Sigma\Delta$-ADC.

10. The X-ray imaging device according to claim 5, wherein the voltage sampling unit and/or the detector comprises a filter unit for generating m data streams composed of sampling values that belong to analogous sampling intervals of different observation periods.

11. The X-ray imaging device according to claim 1, wherein it comprises a spectral discrimination module for determining the line integrals $$A_j = \int_L a_j(\underline{r}) \cdot d\underline{r}$$

for a model function $$\mu(E, \underline{r}) = \sum_j f_j(E) \cdot a_j(\underline{r})$$

of the attenuation coefficient $\mu$ in an object located in an X-ray path L between X-ray source and detector, wherein E is the X-ray photon energy, $\underline{r}$ is the location inside the object, and $f_j$ are given functions.

12. The X-ray imaging device according to claim 1, wherein the device comprises a reconstruction module for calculating the attenuation coefficient $\mu$ in an object located in an X-ray path between X-ray source and detector from X-ray projections of this object taken from different projection directions.

13. The device of claim 11, wherein the impulse response has a boxcar shape.

14. The device of claim 1, wherein the tube spectrum model is equal to the continuous-time model of the tube voltage of the X-ray source multiplied with the tube spectrum model.

15. The device of claim 1, wherein the X-ray source is switched between at least two different voltages, and a waveform of a tube voltage switching is symmetric.

16. The device of claim 15, wherein there is no synchronization between the voltage switching and the X-ray detector.

17. A method for the generation of spectrally resolved X-ray images of an object, comprising the steps of
emitting X-rays with an energy spectrum that varies continuously during a given observation period;
producing a plurality of $m \geq 2$ radiation sampling values that are indicative of the amount of X-radiation measured in a given measurement region during different sampling intervals within the observation period;
estimating effective energy spectra of the emitted X-rays that are associated to said sampling intervals, wherein the effective energy spectra is estimated by folding a tube spectrum model, which is generated based on a continuous-time model of a tube voltage of the X-ray source combined with a tube spectrum model, with an impulse response of the detector.

18. The method of claim 17, wherein the tube spectrum model is equal to the continuous-time model of the tube voltage of the X-ray source multiplied with the tube spectrum model.

19. The method of claim 18, wherein the X-ray source is switched between at least two different voltages, and a waveform of a tube voltage switching is symmetric.

20. The method of claim 19, wherein there is no synchronization between the voltage switching and the X-ray detector.

* * * * *